US005669059A

United States Patent [19]

Carden

[11] Patent Number: 5,669,059
[45] Date of Patent: Sep. 16, 1997

[54] METAL MATRIX COMPOSITIONS AND METHOD OF MANUFACTURING THEREOF

[75] Inventor: Robin A. Carden, Costa Mesa, Calif.

[73] Assignee: Alyn Corporation, Irvine, Calif.

[21] Appl. No.: 536,695

[22] Filed: Sep. 29, 1995

Related U.S. Application Data

[62] Division of Ser. No. 183,728, Jan. 19, 1994, Pat. No. 5,486,223.

[51] Int. Cl.$^6$ .................................................. B22F 1/00
[52] U.S. Cl. ............................ 419/12; 419/23; 419/28; 419/32; 419/42
[58] Field of Search .............................. 419/12, 23, 28, 419/32, 42

[56] References Cited

U.S. PATENT DOCUMENTS

| | | |
|---|---|---|
| 3,178,807 | 4/1965 | Bergmann . |
| 3,591,362 | 7/1971 | Benjamin . |
| 4,104,062 | 8/1978 | Weaver ............................ 75/238 |
| 4,605,440 | 8/1986 | Halverson et al. . |
| 4,623,388 | 11/1986 | Jatkar et al. . |
| 4,661,154 | 4/1987 | Faure . |
| 4,702,770 | 10/1987 | Pyzik et al. . |
| 4,749,545 | 6/1988 | Begg et al. . |
| 4,793,967 | 12/1988 | Pryor et al. . |
| 4,894,088 | 1/1990 | Yamaguchi et al. . |
| 4,941,918 | 7/1990 | Horikoshi et al. . |
| 4,943,320 | 7/1990 | Pechnik et al. . |
| 4,946,500 | 8/1990 | Zedalis et al. . |
| 4,961,778 | 10/1990 | Pyzik et al. . |
| 4,981,643 | 1/1991 | Siemers et al. . |
| 5,006,417 | 4/1991 | Jackson et al. . |
| 5,034,282 | 7/1991 | Hribernik et al. . |
| 5,039,633 | 8/1991 | Pyzik et al. . |
| 5,045,278 | 9/1991 | Das et al. . |
| 5,114,505 | 5/1992 | Mirchandani et al. . |
| 5,128,213 | 7/1992 | Tanaka et al. . |
| 5,273,569 | 12/1993 | Gilman et al. . |
| 5,372,775 | 12/1994 | Hayashi et al. . |
| 5,401,338 | 3/1995 | Lin . |
| 5,435,825 | 7/1995 | Kusui et al. . |

*Primary Examiner*—Charles T. Jordan
*Assistant Examiner*—Anthony R. Chi
*Attorney, Agent, or Firm*—Cooper & Dunham LLP

[57] ABSTRACT

An improved metal matrix composite which, in a preferred embodiment disclosed herein, utilizes boron carbide as the ceramic additive to a base material metal. The metal matrix composite of the present invention begins with the preparation of the boron carbide powder by particle size selection in a jet mill. The resulting powder and metal powder are then mixed by blending of powder of all the various elements such as by means of a conventional blender to uniformly mix powdered substances and avoid stratification and settling. After the particles have been sufficiently mixed, they are degassed and then placed into a die and then into a cylindrical container where the particulates are subjected to extremely high pressures transforming the elements into a solid ingot. It is from these ingots that the extrusion tubes or other articles of manufacture may then be made.

6 Claims, No Drawings

METAL MATRIX COMPOSITIONS AND METHOD OF MANUFACTURING THEREOF

This is a division of application Ser. No. 08/183,728 filed Jan. 19, 1994 now U.S. Pat. No. 5,486,223.

BACKGROUND OF THE INVENTION

1. Field of the Invention

The present invention relates generally to metal matrix compositions. Such composites comprise one or more base material metals such as for example, aluminum, titanium or magnesium, to which is added a selected percentage of ceramic materials which alter the properties of the base material metal in a positive manner. Strength, hardness and drawability are increased. Drawability facilitates fabrication of various articles of manufacture from such composite materials. More specifically, the present invention pertains to an improved metal matrix composite which, in a preferred embodiment, uses boron carbide as the added ceramic material. The composites result from a novel method of manufacture producing a composite which is lighter, stronger, stiffer and which has a higher fatigue strength than other available alloys of the base material metal and which is also lighter, stronger, stiffer and which has a higher fatigue strength than prior art metal matrixes, composites and particularly those metal matrix composites which are of comparable cost.

2. Prior Art

In recent years metal matrix compositions or composites have become popular materials for a variety of applications. This new family of materials has become popular because of improvements in stiffness, strength and wear properties. Basic metal matrix composites are made typically with aluminum, titanium or magnesium as the base material metal. Then certain percentages of ceramics are added. Typical ceramics are boron carbide, silicon carbide, titanium diboride, titanium carbide, aluminum oxide and silicon nitride. Most known metal matrix composites are made by introducing the ceramics into the molten metal. In large production runs of metal matrix composites, the ceramic reinforcement must be wetted by the liquid metal to facilitate incorporation of the reinforcement into the melt. In those metal matrix composites using silicon carbide and aluminum, the silicon carbide is thermodynamically unstable in molten aluminum which leads to the formation of aluminum carbide at the interface and increased concentration of silicon in the material matrix during the solidification process. This interface reaction is believed to have detrimental effects on the mechanical properties of the resulting composite by reducing the interface strength and changing the composition.

Recently, powder metalurgy consolidation has emerged as a competing method of fabricating metal matrix composites by consolidating the powders by means of hot pressing and conventional powder metalurgy operations with vacuum sintering to achieve a high density green body. By following certain isopressing and sintering techniques, a 99% theoretical dense billet can be achieved.

In the present invention it has been found that the most desirable ceramic candidate for metal matrix composites is boron carbide. Boron carbide is the third hardest material known and the hardest material produced in tonage. Boron carbide powders can be formed by a variety of reactions including the carbon reduction of any of several boron-oxygen compounds including boric oxide, boric acid, borax, boracite as well as by the direct combination of the elements.

Usually most commercial boron carbide is produced in arc furnaces. Boric acid is added together with carbon in the form of coke and heated to very high temperatures. An electric arc is maintained between graphite electrodes inside a furnace. The synthesis reaction is accompanied by the release of large volumes of carbon monoxide. Venting and disposal of the carbon monoxide gas constitutes a major design consideration. Boron carbide is also the lightest Of all of the ceramics typically used in metal matrix composite technology, but it is very hard and expensive. Its hardness limits its extrudability. Thus it would be highly advantageous if it were possible to produce an improved metal matrix composite which utilizes an advanced ceramic such as boron carbide but which, unlike the prior art, results in an extrudable composite material which allows easy fabrication of various articles of manufacture so that such resulting articles have the specific strength and stiffness improvements as compared to equivalent articles of manufacture using only the base material metals.

SUMMARY OF THE INVENTION

The present invention comprises an improved metal matrix composite which, in a preferred embodiment disclosed herein, utilizes boron carbide as the ceramic additive to a base material metal. The fabrication process is unlike that of a number of other metal matrix composites because it is not made through molten processes. More specifically, instead of melting the boron carbide with the aluminum, nickel, zinc, titanium or other base material metal, the metal matrix composite of the present invention begins with the blending of powder of all the various elements such as by means of a jet mill which is basically an air blaster used to uniformly mix powdered substances and avoid stratification and settling. After the particles have been sufficiently mixed, they are directed into a die and then into a cylindrical container where the particulates are subjected to extremely high pressures transforming the elements into a solid ingot. It is from these ingots that the extrusion tubes or other articles of manufacture may then be made. The resulting advanced metal matrix composite is in the boron carbide embodiment of the invention, 60% lighter, 30% stronger, 40-45% stiffer and 50% higher in fatigue strength than any of the top of the line 7000 series aluminum alloy materials. In addition, the inventive material is 7-8% lighter, 26% stronger, 5% stiffer, and has 35-40% greater fatigue strength than most popular metal matrix composites available in the prior art.

In the preferred embodiment disclosed herein the base material metal is preferably an aluminum alloy or titanium alloy provided in powder form and preferably being approximately 97% pure with the balance of the material comprising various trace metals such as chromium, copper, iron, magnesium, silicon, titanium and zinc. The boron carbide powder is preferably 99.5% pure boron carbide having a particulate size in the range of 2-19 microns with a mean or average size of approximately 8.4 microns. In one typical embodiment of the invention, the metal base material was selected from an aluminum alloy 6061T-6 to which was added approximately 12% by weight, the aforementioned boron carbide powder to which was added silicon in an amount of 0.1-0.4%, iron in the amount of 0.05-0.4% and aluminum in an amount of 0.05-0.4%. The underlying boron carbide material was approximately 77% boron content and 22% carbon content. A metal matrix composite made from the aforementioned materials in accordance with the fabrication process of the present invention to be described hereinafter, resulted in a composite material which exhibited an ultimate tensile strength of 70.1, a yield strength of 61.2, and a drawability factor of 71.9 on a scale of 0–100. Furthermore, the resulting material is approximately as hard as chromoly steel but has a density which is even lower than aluminum alloy. Importantly, the material of the present invention is readily extrudable. In a preferred extrusion step, ingots of the metal matrix composites of the present invention are extruded through a titanium diboride die bearing material which exhibits a significant increase in die insert life. Furthermore, the present invention is readily weldable. In fact, the coated boron carbide particulates of the material disclosed herein tend to flux and move into the weld pool which creates a very strong weld joint. Thus the present invention is not only highly suited for the manufacture of various shaped articles, but is also suited for interconnecting such articles by conventional welding processes as will be hereinafter more fully explained.

OBJECTS OF THE INVENTION

It is therefore a principal object of the present invention to provide an improved metal matrix composite material which exhibits certain advantageous properties and manufacturability conducive to the fabrication of certain articles of manufacture having improved characteristics such as reduced weight, higher strength and increased hardness.

It is an additional object of the present invention to provide an improved metal matrix composite material which is especially adapted for use as structural members in lightweight applications such as bicycle frames and the like while retaining or improving the strength and hardness at the same relative cost of comparable materials used in similar structures.

It is still an additional object of the present invention to provide a metal matrix composite material which is stiffer and lighter than aluminum while being as hard as steel and extremely fracture resistant while also being extrudable and weldable, thus permitting the fabrication of extremely high strength, lightweight structural members at reasonable cost.

It is still an additional object of the present invention to provide a method for manufacturing an improved metal matrix composite material to result in a material having superior hardness, strength and density characteristics while being extrudable and weldable for use in the manufacture of a variety of structural members which may be readily connected to one another such as in bicycle frames, aircraft parts, tooling, sporting equipment, eyewear, automotive parts, electronic parts, furniture and medical equipment.

DETAILED DESCRIPTION OF A PREFERRED EMBODIMENT

The preferred embodiment of the present invention uses aluminum alloy as a base material metal and boron carbide as the added ceramic material. In the preferred embodiment of manufacture the aluminum alloy is provided in the form of a metal powder which is blended with jet milled boron carbide particulates that have been processed and have certain chemical and particulate size attributes. The boron carbide is preferably at least 99.5% pure and has a 2–19 micron particle size with an average particle size of about 8.4 microns. Included in the boron carbide powder is 0.1–0.4% silicon, 0.05–0.4% iron and 0.05–0.4% aluminum. Trace amounts of magnesium, titanium and calcium may also be provided. Two exemplary semi-quantitative analyses of acceptable boron carbide powders for use in the present invention are shown hereinbelow in Tables I and II.

TABLE I

| B | 77.3% |
|---|---|
| Si | 0.37 |
| Mg | 0.0016 |
| Fe | 0.026 |
| Al | 0.18 |
| Cu | 0.0021 |
| Ti | 0.0088 |
| Ca | 0.0049 |
| Other elements | nil |
| $C, O_2$ | (BAL) |

TABLE II

| B | 77.7% |
|---|---|
| Si | 0.14 |
| Mg | 0.0017 |
| Fe | 0.074 |
| Al | 0.13 |
| Cu | ND 0.0002 |
| Ti | 0.017 |
| Ca | 0.0048 |
| Other elements | nil |
| $C, O_2$ | (BAL) |

The addition of small amounts of pure aluminum, silicon and iron to the arc furnace during the production of boron carbide, such as by the reaction of boric acid and carbon, has been found to improve the boron carbide for use in this metal matrix composite. These metal elements do not go out of solution. They stay in the boron carbide and provide a chelating opportunity for the base material aluminum. These additional metals form an inter-metallic chemical bond with the main metal alloy. However, it will be understood that the aforementioned additions of pure aluminum, silicon and iron, may not be the only metals which can be used for the aforementioned purpose. By way of example, virtually any low temperature reacting metal that forms an inter-metallic phase below the processing temperature of the metal matrix composite ingot, would be useable in the present invention for the purpose indicated. The typical relative weight contributions of the boron carbide powder and base material metal powder is 12–15% of the former and 85–88% of the latter depending upon the specific characteristics desired for the finished product.

After the boron carbide has been jet milled to the selected particulate size and with the aluminum alloy powder blended together in a double chamber "V" blender, for two and one-half hours at 20 to 30 RPM in an inert gas, the powders are degassed at 200 degrees Centigrade for one hour in a vacuum of −5 to −8 Torr and then placed in a latex bag and isopressed at 65,000 psi. The isopress bag resembles the shape of the ingot that is to be extruded. The latex bag is degassed and clamped off. The maximum pressure is held for at least a one minute soak. The resulting ingots are removed from the bag and placed into a vacuum furnace to undergo a sintering cycle in accordance with the following preferred embodiment of the process of the present invention.

First, the ingots are heated from room temperature to 300 degrees Centigrade over a twenty minute ramp period during which time binder and water are burned off. The ingots are then heated to 450 degrees Centigrade over a fifteen minute ramp period during which the remaining binder is burned off. The ingots are then heated to 625 degrees Centigrade over a forty minute ramp period during which the temperature increases accordingly. At 625 degrees Centigrade the ingot is held and soaked at that temperature for 45 minutes during which close grain boundaries are formed. The ingot is then cooled from 625 degrees Centigrade to 450 degrees Centigrade over a twenty minute period by means of a nitrogen gas backfill. Finally, the ingots are cooled to room temperature at a rate not faster than 40 degrees Centigrade per minute again using nitrogen gas. The ingots are then turned down by a metal lathe to bring them into an extruding shape with a typical selected outer diameter of between 3½ and 7 inches to a tolerance of 15,000ths of an inch. The ingots are then available for extrusion.

Extruding the metal matrix composite of the present invention first involves preheating the ingots in a resistance furnace for a minimum period of one hour at 555 degrees Centigrade. This is normally done in two steps. First the ingots are heated to 315 degrees Centigrade in a holding furnace and then heated to a higher temperature and held until the ingot temperature reaches 555 degrees Centigrade. The ingots are then loaded directly into a container or chamber from the furnace. The chamber temperature should preferably be 488 degrees Centigrade. The face pressure within the chamber depends upon the type of extrusion dimensions that are desired. Typically, the pressures used are 15–20% higher than extrusion pressures used for 6061 aluminum ingots. For example, for a 3½ inch outer diameter billet made of the metal matrix composite of the present invention, 3,500 psi peak (break out) pressure is typically used and results in an extruding pressure of about 3,000 psi. The speed of the extrusion could be an average of 15–30 feet per minute and the exit temperature should be 20 degrees Centigrade cooler than the container temperature. The speed of the ram used for the extrusion should run 3½ inches every minute on a typical 3½ inch outer diameter ingot.

Although the present invention may be extruded in conventional dies, it has been found that for maximum die insert life, a die bearing material made of titanium diboride is preferred. The titanium diboride die bearing material is preferably hot pressed and then electrodischarge machined to the appropriate size. A small amount of boron carbide may be used to increase the hardness of the die. Typically, the die is made of 99.5% pure titanium diboride in an amount equal to 92–98% by weight, the remaining fraction being 99.5% pure boron carbide having particulate sizes less than 10 microns. The hot press cycle for manufacture of the die bearing material is preferably done at 1,800 degrees Centigrade using a 3,500 psi pressure with the pressure and temperature maintained until a zero drop in ram travel is obtained.

The extruded metal matrix composite provides the greatest benefit if it is heat treated using a T6-type heat treatment which comprises two hours at 530 degrees Centigrade with a cold water quench and an artificial aging at 177 degrees Centigrade for ten hours. All welding however has to be accomplished before heat treatment is applied. Unlike other metal matrix composites which contain silicon carbide and aluminum oxide where welding can be a problem, the metal matrix composite of the present invention is readily weldable. Other metal matrix composites form aluminum carbides as brittle components of a weld. Aluminum carbides are formed from the chemical reaction of aluminum and silicon carbide. Because of the surface area of the aluminum oxide particulates and metal matrixes, clumping and dewetting occurs. These brittle components and particulates clump together thereby greatly decreasing the strength of a weld body. The metal matrix composite of the present invention does not have these problems. The coated boron carbide particulates tend to flux and move into the weld pool which creates a very strong weld joint. Because boron carbide particulates have a melting point of 2,450 degrees Centigrade, the boron carbide is chemically inert at aluminum processing temperatures.

Depending upon the ratio of boron carbide to aluminum and also depending upon the particular aluminum alloy used as the base material metal, the resulting material has a density of approximately 2.69 grams per cubic centimeter which is lower than aluminum 6061. The resulting material also has an ultimate strength of from 70–104 ksi, a yield strength of 61–98 ksi, and is extremely fracture resistant and more predictable than other composites. Furthermore, the resulting material of the present invention has a hardness which is comparable to that of titanium and chromoly steel, but a density which is roughly a third of steel and roughly 60% of titanium.

Two advantageous products made from the metal matrix composite of the invention are bicycle frames and golf club heads. Bicycle frames made from extruded and welded tubing of the inventive material are lighter, stiffer and stronger than comparable bicycle frames made of more conventional materials such as aluminum, steel or titanium. In golf clubs, the lower density of the inventive material allows for thicker walled heads, better weight distribution, balance and aerodynamics. Furthermore, a larger "sweet spot" is possible in tournament legal clubs.

Having thus described a preferred embodiment of the material composition and method of fabrication of the present invention, what is claimed is:

1. A method of fabricating a metal matrix composite comprising the following steps:

a) blending powders of a bore material metal, boron carbide and at least one metal additive having an inter-metallic phase temperature below the melting point of said base material metal; wherein said boron carbide constitutes about 10% to 16% of the powders by weight and said additive constitutes less than about 1.5% of said powders;

b) degassing said blended powders;

c) isopressing said blended powders at a pressure of at least 65,000 psi;

d) heating said isopressed powders up to at least 625 degrees Centigrade over a selected period of time;

e) configuring said isopressed and sintered powders to the desired shape; and f) heat treating the resulting shape of step e).

2. The metal matrix composite fabrication process recited in claim 1 wherein step e) is performed by extruding said isopressed and sintered powders at a selected temperature and pressure through an extrusion die of selected dimensions.

3. The metal matrix composite fabrication process recited in claim 1 wherein said base material metal is taken from the group consisting of: aluminum, titanium, alloys of aluminum and alloys of titanium.

4. The metal matrix composite fabrication process recited in claim 1 wherein said at least one metal additive is taken from the group consisting of: aluminum, silicon, iron and titanium.

5. The metal matrix composite fabrication process recited in claim 1 wherein said boron carbide powder has a particulate size in the range of 2 to 19 microns and an average particulate size of about 6.5 microns.

6. The metal matrix composite fabrication process recited in claim 2 wherein said extrusion die has a liner structure comprising titanium diboride and boron carbide.

\* \* \* \* \*